United States Patent
Hansen

(10) Patent No.: US 6,657,713 B2
(45) Date of Patent: *Dec. 2, 2003

(54) INSTRUMENT FOR SELECTING AND DEPOSITING MULTICELLULAR ORGANISMS AND OTHER LARGE OBJECTS

(75) Inventor: W. Peter Hansen, Canaan, NY (US)

(73) Assignee: Union Biometrica, Inc., Somerville, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/991,394

(22) Filed: Nov. 21, 2001

(65) Prior Publication Data

US 2002/0033939 A1 Mar. 21, 2002

Related U.S. Application Data

(63) Continuation of application No. 09/378,634, filed on Aug. 20, 1999.
(60) Provisional application No. 60/097,505, filed on Aug. 21, 1998, and provisional application No. 60/111,723, filed on Dec. 10, 1998.

(51) Int. Cl.[7] .................................................. B07C 5/36
(52) U.S. Cl. ........................ 356/237.1; 209/639; 356/72
(58) Field of Search ........................... 356/72, 73, 625, 356/635, 237.1; 209/639

(56) References Cited

U.S. PATENT DOCUMENTS

| 3,489,277 A | 1/1970 | Silverman .................... 209/639 |
| 4,021,117 A | 5/1977 | Göhde et al. .................. 356/39 |

(List continued on next page.)

FOREIGN PATENT DOCUMENTS

| EP | 0 422 616 A2 | 10/1990 |
| EP | 0 626 455 A1 | 5/1993 |
| GB | 1 318 720 | 11/1970 |
| JP | 62229045 | 10/1987 |
| JP | 04204254 | 11/1990 |
| JP | 04001568 | 1/1992 |
| JP | 06109617 | 4/1994 |
| WO | 00/63427 | 10/2000 |

OTHER PUBLICATIONS

PCT International Search Report dated Oct. 19, 1999 for PCT/US99/19035, International filing date Aug. 20, 1999.

"Machine for rapidly counting and measuring the size of small nematodes," L. Byerly et al., *Rev. Sci. Instrum.*, vol. 46, No. 5, May 1975.

(List continued on next page.)

*Primary Examiner*—Richard A. Rosenberger
(74) *Attorney, Agent, or Firm*—Choate, Hall & Stewart; Brenda H. Jarrell; Charles E. Lyon

(57) ABSTRACT

An instrument for analyzing and dispensing objects larger than about 70 μm in diameter is based on a flow cytometer with a novel fluidic switch arrangement for diverting a portion of a sample stream in response to detector signals in a flow cell. The instrument is particularly adapted for dispensing multicellular test organisms like nematodes or large microspheres for use in screening large libraries of potential pharmaceutical agents. Hydrodynamic focussing is used to center and align the objects in the flow cell. The objects pass through a sensing zone where optical or other characteristics of the objects are detected. The detector signals are processed and used to operate a fluidic switch that is located downstream from the sensing zone. The fluid stream containing the detected objects emerges from the flow cell into air where a fluid stream controlled by the fluidic switch diverts portions of the stream containing no sample objects or sample objects not meeting predetermined characteristics. The undiverted sample stream deposits selected sample objects into a plurality of containers.

51 Claims, 7 Drawing Sheets

U.S. PATENT DOCUMENTS

| | | | |
|---|---|---|---|
| 4,056,324 A | 11/1977 | Göhde | 356/246 |
| 4,225,229 A | 9/1980 | Gohde | 356/39 |
| 4,284,412 A | 8/1981 | Hansen et al. | 23/230 |
| 4,325,706 A | 4/1982 | Gershman et al. | 23/230 |
| 4,756,427 A | 7/1988 | Göhde et al. | 209/3.1 |
| 5,180,065 A | 1/1993 | Touge et al. | 209/639 |
| 5,638,961 A | 6/1997 | Satake et al. | 209/639 |

OTHER PUBLICATIONS

"The Life Cycle of the Nematode *Caenorhabditis elegans*, II. A Simplified Method for Mutant Characterization," L. Byerly et al., *Developmental Biology* 51, 34–49 (1976).

"An Improved Instrument for the Rapid Counting and Simultaneous Two Parameter Measurement of Small Nematodes," C.J. Barinaga et al., *International Worm Meeting*, Abstract 28, 1981.

"Cytokinetic investigation of lung tumors using the anti–bromodeoxyuridine (BudR) monoclonal antibody method: comparison with DNA flow cytometric data," L. Teodori et al., *Int J Cancer* Jun. 15, 1990;45(6):995–1001.

"Flow–cytometry analysis of sheep–nematode egg populations," D. Kerboeuf et al. *Parasitology Research* 82 (4). 1996. 358–363 (Abstract).

"Large size range flow cytometry of phytoplankton," G. Dubelaar, article undated, printed from web page Dec. 2, 1997.

"EurOPA: a new flowcytometer of fytoplankton," L. Boddy et al., article undated, copyright 1996 AquaSense, the Netherlands, printed from web page Dec. 2, 1997.

"EurOPA flow cytometer sorter system," G. Dubelaar, article undated, printed from web page Dec. 2, 1997.

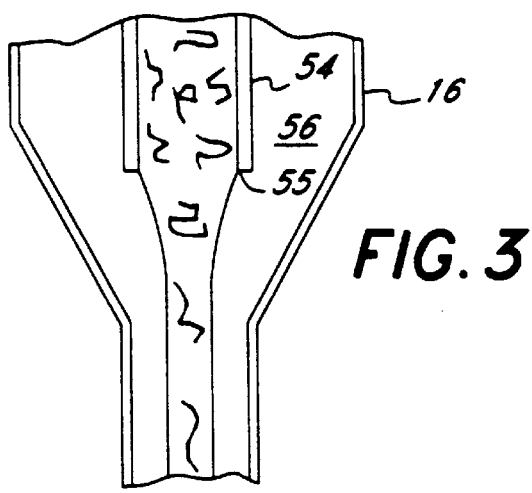
FIG. 3
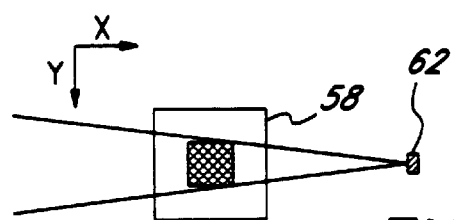
FIG. 5A
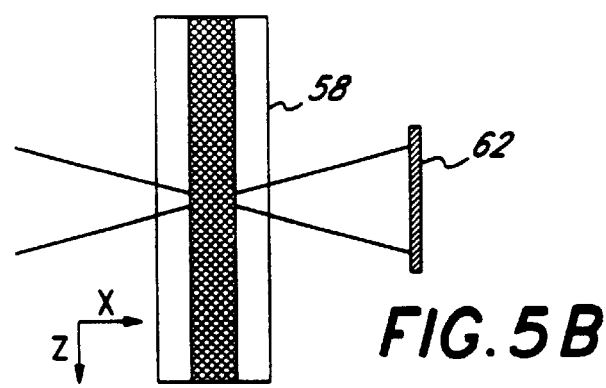
FIG. 5B
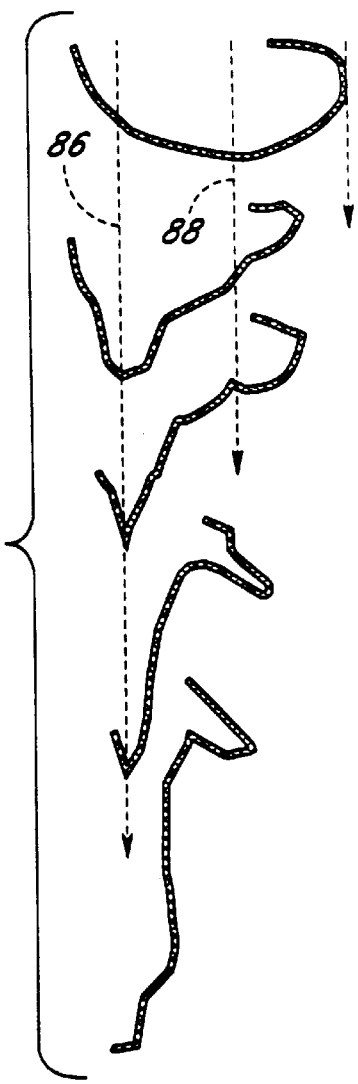
FIG. 4
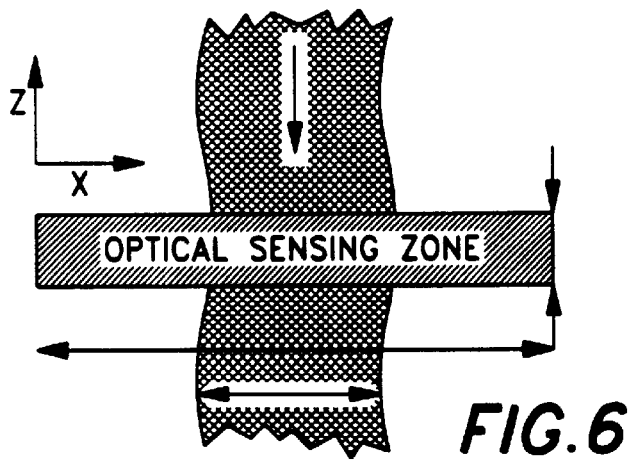
FIG. 6
FIG. 7

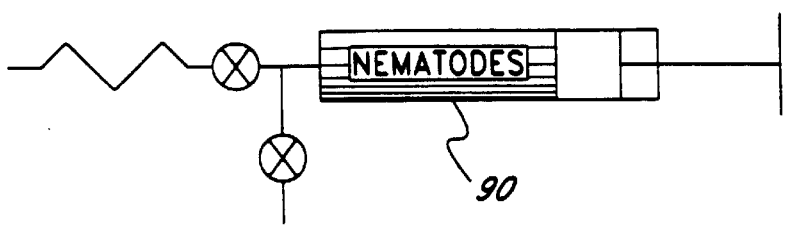
FIG. 8A  FIG. 8B
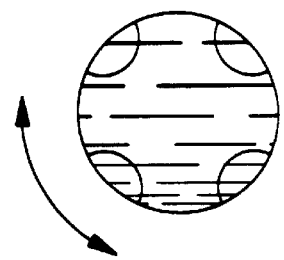
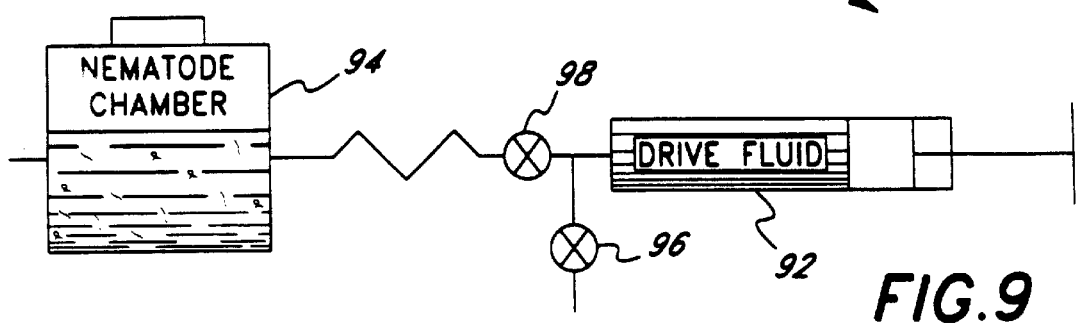
FIG. 9
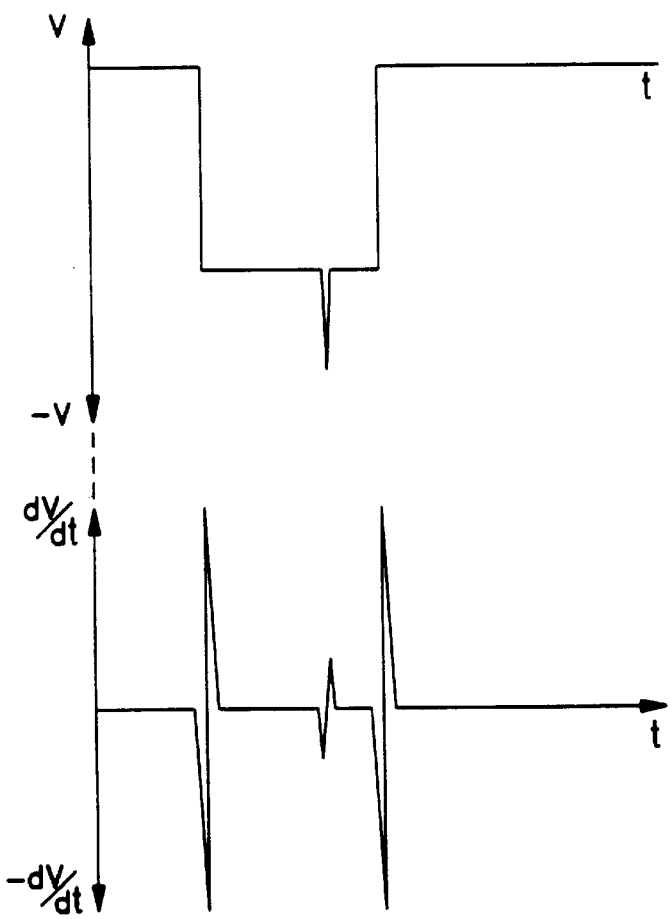
FIG. 10A
FIG. 10B

INSTRUMENT FOR SELECTING AND DEPOSITING MULTICELLULAR ORGANISMS AND OTHER LARGE OBJECTS

The present application is a continuation of Application Ser. No. 09/378,634 filed Aug. 20, 1999 which claims the benefit of U.S. Provisional Patent Application No. 60/097,505 entitled "Fluid Switch Controlled Machine for Selecting and Depositing Multicellular Organisms," filed Aug. 21, 1998 and U.S. Provisional Patent Application No. 60/111,723 entitled "Nematode Sorting Machine," filed Dec. 10, 1998; priority is claimed from these applications both of which are incorporated herein by reference.

BACKGROUND OF THE INVENTION

1. Field of the Invention

The present application concerns high-speed mechanisms for automatically identifying and physically selecting multicellular organisms or other large objects with predetermined characteristics from mixed populations and depositing them in discrete locations.

2. Description of Related Art

Intact multicellular organisms, such as nematodes, fruit fly larvae, or zebrafish embryos are frequently used as model systems to help understand the function of human genes that have been implicated to play a role in disease. Human gene homologues have been identified in these model organisms and mutations have been induced specifically in those gene homologues. Such mutations frequently result in an easily observable phenotypic change in the model organism, and it has been shown that certain mutants respond to pharmacological compounds with a measurable mode of action. Mutants of intact organisms are now used as a new class of in vivo drug screens for combinatorial pharmacological compound libraries. By using these organisms, one can identify targets for drug intervention without the need to completely understand complex biochemical pathways between the genotype and the phenotype. In addition solid state combinatorial chemical approaches are now being utilized to produce these drug libraries; the end result is that the sample chemicals to be tested are present on solid microspheres usually between 100 and 500 $\mu$m in diameter. These solid state techniques greatly speed the preparation of the sample compound library but necessitate a method to accurately select and dispense these microspheres for testing purposes.

The historic approach to modeling diseases in multicellular organisms has been to make morphological or behavioral mutants with substantial phenotypic defects. The intent of such research is to produce a mutant that resembles or models a disease state so that new therapeutics can be screened without using human "guinea pigs." In fact, considering the current prevalence of animal rights activists, the safest approach is to entirely eschew the use of mammals for testing purposes. The goal, then, has been to observe these model disease defects and their interaction with candidate therapeutics objectively and with high sensitivity. Unfortunately, this goal has been not often met. The closest approach to reaching the goal has been to devise "live-dead" assays that can be carried out in microwell arrays using optical readout systems. The plan is to dispense individual organisms into microwells, add the candidate therapeutic and optically detect the response. If the candidate therapeutic is present on a microsphere, then the microsphere must also be accurately selected and dispensed.

The exposure of model organism mutants to diverse pharmaceutical compound libraries, even when the mutation has not been linked to a human gene homologue also helps define gene function. The addition of such functional genomic techniques to the repertoire of molecular biology and biochemistry methods is leading to a significant increase in speed in the pharmaceutical discovery process. Investigators annotate pharmaceutical drug libraries for toxicity, non-specific activity, or cell membrane permeability, etc. by observing their behavior in intact organisms. This way, potential new therapeutics that show toxicity or harmful results can be discarded early without wasting valuable resources.

The soil nematode *Caenorhabditis elegans*, has become a particularly important multicellular organism for these types of tests because its anatomy, development, behavior and genome, is more completely understood than that of any other animal. *C. elegans* is a small metazoan animal composed of only 959 cells, each generated from a single zygote cell through a completely known cell lineage. This small number of cells nonetheless exhibits a diversity of cell types that typifies more complex animals, including skin, muscle, gut and nerve cells.

The genes of *C. elegans* are easily accessed through powerful classical and molecular genetic tools. The sequencing of the *C. elegans* genome is also more advanced than that of any other animal and is a model for the Human Genome Project. Although most human disease genes that have been identified and cloned based on chromosomal position have no known function, the vast majority of these as well as most other human genes have *C. elegans* homologs. These homologs can be rapidly analyzed using the above-mentioned approach to elucidate the functional biology of the homologous human gene.

A striking conclusion from studies of *C. elegans* is that the cellular and molecular mechanisms that operate in this nematode are strikingly similar to those that operate in more complex animals, including man. These similarities are so great that homologous human genes can function in nematodes and nematode genes can function in mammalian cells. Researchers are therefore using this nematode for numerous types of experiments related to the development of pharmaceutical agents for use in humans and other higher animals.

Despite the potential power and speed of using multicellular organisms like *C. elegans* current programs for rapid pharmaceutical drug discovery of not employ high-speed preparation techniques. As an example, with today's molecular biology techniques, a large laboratory can produce deletion mutations in multicellular organisms at a rate of 20 to 30 per month. To evaluate the effect of a chemical compound library (that frequently may contain 100,000 or more members) on a class of mutated organisms, one must first manipulate and deposit a precise number of organisms in the same development stage into a container, such as the wells of a microtiter plate array. Organisms of different development stage must be excluded since they would convolute the measured response.

Using slow, manual methods, the selection and deposition of organisms of the proper type is a bottleneck for the entire process of pharmaceutical discovery. If the test compounds are present as microspheres, then the accurate selection and dispensing of microspheres adds an additional bottleneck. Furthermore, manual methods rely on pipettes that dispense accurate volumes of fluid and not accurate numbers of organisms. In many studies where reproduction rate is altered by the mutation, it is necessary to begin the study of the effect of a compound from the combinatorial library with an exact, and known number of multicellular organisms in each well. Any selection system based on volume is liable to dispense inaccurate numbers of organisms because precisely uniform suspensions of organisms are impossible to maintain. In the same way if the test compounds are available as microspheres it is extremely difficult to place a controlled number of microspheres in each well. Further, the microsphere population may be mixed so ultimate results require not only precise counting but selection of microspheres—clearly an impossible task for simple pipettes.

Flow cytometers have operational characteristics that make them adaptable to the problems of automating the selection and deposition of multicellular organisms and other large objects such as microspheres. Flow cytometers have been used to count the number of nematodes in a given volume of fluid. Such a device was described by Byerly et al (Byerly, L., R. C. Cassada, and R. L. Russell, "Machine for Rapidly Counting and Measuring the Size of Small Nematodes", Rev. Sci. Instrum. Vol 46, No. 5, May 1975) where the flow cytometer utilized sheath flow to orient the nematodes along the direction of flow so that their length could be measured and organism-by-organism counts could be made by an electrical impedance method similar to that used in a commercial Coulter® counter. A flow cytometer for working with multicellular organisms is not limited to using an impedance sensor, but can be a more modem optically sensing flow cytometer.

For example, an optical flow cytometer for analyzing elongate organisms such as plankton with widths of 500 $\mu$m and lengths over 1000 $\mu$m has been described in a number of published articles such as Peeters, J. C., G. B. Dubelaar, J. Ringelberg, and J. W. Visser, "Optical Plankton Analyser: a Flow Cytometer for Plankton Analysis, I: Design Considerations" Cytometry September 10 (5): 522–528 (1989); and Dubelaar, G. B., A. C. Groenwegen, W. Stokdijk, G. J. van den Engh, and J. W. Visser, "Optical Plankton Analyser: a Flow Cytometer for Plankton Analysis, II: Specifications", Cytometry September 10 (5): 529–539 (1989). The size range of the plankton used in these optical flow cytometers is similar to that encountered with nematodes, fruit fly larvae, and zebrafish embryos. In all of these references, the multicellular organisms were merely analyzed but were not selected and deposited. Similarly, analysis of large microspheres with flow cytometers is routine as long as the cross-sectional area of the flow cell is sufficient to accommodate the microsphere.

Selection and deposition of non-multicellular organisms and other small objects with flow cytometers is well known. The method used to select and deposit specific organisms or objects (e.g. microspheres) on command from the flow cytometer consists of a mechanism to switch the direction of the flowing stream of organisms or objects that emerges from the flow cell of the flow cytometer so that analyzed objects can be specifically deposited in a microwell plate or similar container. Switching is performed at a fixed delay time after the flow cytometer has identified a desirable organism. The delay is typically in the time scale of a millisecond to tens of milliseconds. The most common method found in commercial cell sorters is electrostatic diversion of desired objects once they have emerged from an exit port in the flow cell into air. Electrostatic diversion is accomplished by charged plates that operate on a stream of droplets.

However, electrostatic cell sorters are designed specifically for single cells and are not useful for sorting large objects such as nematodes, fruit fly larvae, zebrafish or large microspheres. This is because the flow cell of an electrostatic cell is mechanically vibrated at frequencies of tens of kilohertz to mechanically break the fluid stream into (charged or uncharged) droplets in air that are of the order of 50 $\mu$m in diameter. This size droplet is optimal for typical single cells with diameters of 5 $\mu$m to 30 $\mu$m, but it is much smaller than most multicellular organisms, which are typically of the order of 1 mm in length. The mechanical vibration step and the subsequent breakup of the stream into small droplets is typically lethal to multicellular organisms. The vibration frequency of an electrostatic cell sorter is not variable; therefore, one cannot change the droplet size to accommodate multicellular organisms. Furthermore the entire flow cell always vibrates at this frequency, making it impossible to create single droplets on command.

In the case of large microspheres used in combinatorial chemistry there is no worry that mechanical vibration will damage the microsphere. Nevertheless, electrostatic sorters are unable to effectively select and deposit such large objects. This is a result of the geometry used with the electrostatic deflection plates. At the voltages commonly used static charge results in a deviation of only a few degrees. It is impossible to produce greater deviations by increasing the voltages because arching will occur. Adequate deviation to separate selected from rejected droplets is achieved by allowing the stream to fall a sufficient distance beyond the charged plates. In the case of the typical 50 $\mu$m droplet the droplets fall an additional 2.5 cm beyond the deflection plates. If the droplet size is doubled to 100 $\mu$m (still insufficient to accommodate a 100 $\mu$m combinatorial chemistry microsphere), the larger droplet has greatly increased mass which means that the angle of deviation is smaller; therefore, a longer fall distance is necessary to produce adequate deflection (i.e., the deflection angle is smaller). The net result is that 100 $\mu$m droplets require a fall distance of 20 cm. With such a large fall distance tiny instabilities in the flow stream are magnified into appreciable deflections. The microwells of the plates in current use may be on the order of one to a few millimeters in diameter. With a 20 cm fall distance current electrostatic sorters are unable to accurately hit such a small target. The problem becomes even more acute when the droplet size is increased farther to accommodate 400 $\mu$m microspheres or multicellular organisms. With a droplet size of one-millimeter (the size necessary to cushion a typical nematode) the fall distance increases to about 125 cm making it totally impossible to deposit droplets in target containers of even several millimeters diameter.

Thus, electrostatic sorters are completely unsuited to multicellular organisms or other large objects. Even if the process does not kill or damage the organism, the deflection geometry makes it impossible to accurately deposit large objects.

SUMMARY OF THE INVENTION

The invention features an instrument for selecting and accurately dispensing multicellular organisms and other large objects. The instrument uses hydrodynamic flow conditions in an alignment chamber to align elongate multicellular sample organisms and center organisms or objects in the center of a fluid flow stream after which they pass single file through a sensing zone which is preferentially within the chamber. In the sensing zone the aligned and centered objects are interrogated preferably by a light beam. Optical detectors receive refracted, reflected, fluoresced and scattered light from the interrogated objects and output corresponding electrical signals. A signal processing computer system uses these signals to choose desired analyzed objects. A first fluid switch downstream of the sensing zone and outside of the chamber is responsive to signals developed by the computer system. When the switch is open, the flow stream containing the objects passes the switch and into a collection container. When the switch is closed, a fluid stream from the switch deflects the flow stream containing the analyzed objects and prevents it from reaching the collection container.

In preferred embodiments, the fluid switch can include a switched source of compressed gas having a gas output directed toward a location downstream from the sensing zone and outside of the chamber. The switched source of compressed gas can include a source of compressed gas and an electrically operated valve, such as a solenoid valve, to interrupt a gas stream from the source of compressed gas. The switched source of compressed gas can be operative to interact with the fluid flow stream carrying objects from the sensing zone with sufficient force to convert the carrier fluid into a droplet spray. A sample source can be operative to supply a fluid carrying a sufficiently low concentration of large sample objects that the objects flow substantially one at a time through the sensing zone. The fluid switch can be responsive to a delayed detection signal from the computer system. The fluid switch can be operative to include only predetermined amounts of fluid with the selected sample object. The computer system can be operative to cause the switch to select one object at a time, with each object being accompanied by a predetermined volume of fluid.

An illumination source can be directed toward the sensing zone, with the detector being an optical detector. The computer system can be operative to determine the length of at least one of the selected objects by measuring the time that the at least one of the objects takes to pass between the detector and the illumination source. The detector can be an on-axis detector, located across the sensing zone along an illumination axis of the illumination source. The detector can be an off-axis detector generally perpendicular to an illumination axis of the illumination source. An on-axis detector can be located across the sensing zone along the illumination axis of the illumination source. The illumination source can be a focused low-power laser. The sensing zone can have a width of about 10–40 $\mu$m. The sensing zone can have a square cross-section. The output opening of the sample source can be separated from the sensing zone by a total conduit volume of less than 500 microliters. A second fluid switch downstream of the first fluid switch and outside of the chamber can dispense the selected objects into different containers.

In another general aspect, the invention features a multicellular organism or large particle dispensing instrument that includes means for aligning the organisms or objects in a fluid stream in a direction parallel to a flow direction of the fluid stream, means for detecting the presence of the organisms or objects in the fluid stream located downstream from the means for aligning, and means for selectively diverting portions of the fluid, with the means for selectively diverting being located downstream from the means for detecting, being outside of any chamber containing the means for aligning and being responsive to the means for detecting.

In preferred embodiments, the multicellular organism and large object dispensing instrument can further include means for redirecting an output of the means for determining relative to a first container to thereby dispense further ones of the organisms into a second container. The means for selectively diverting can be for including only a predetermined amount of fluid with each of the organisms selected.

In a further general aspect, the invention features a method of dispensing multicellular organisms and large objects that includes centering and orienting the organisms or objects in a longitudinal orientation in a chamber, flowing the organisms in the longitudinal orientation through the center of a sensing zone with a carrier fluid, and detecting the presence of the organisms or objects in the sensing zone. At least some of the carrier fluid is diverted by means for diversion based on the step of detecting ones of the organisms or objects and ones of the organisms or objects remaining in portions of the carrier fluid that were not diverted are collected. The means for diversion are disposed outside of the chamber.

In preferred embodiments, the step of diverting can include a step of converting the carrier fluid into a droplet spray. The step of diverting can take place for a predetermined period of time for each of the detected organisms. The method can also include step of illuminating the sensing zone, with the step of detecting light from the step of illuminating. The step of detecting can employ an on-axis detector and an off-axis detector and combine signals from these detectors. The step of centering can include a step of conveying a sheath fluid past a nozzle. The step of conveying can be performed with a maximum Reynolds number of around one hundred. The method can further include a step of sorting the organisms or objects into a plurality of categories after the step of diverting, with the step of collecting placing the organisms or objects in a plurality of different containers. The method can further include the step of exposing the organisms collected in the step of collecting to a pharmaceutical agent, which may be borne by a large object. The step of dispensing the organisms can include dispensing predetermined numbers of nematodes into each of a number of containers. The step of flowing can introduce reference particles along with the nematodes. The step of dispensing can include dispensing only multicellular organisms having a particular characteristic into a given container.

In another general aspect, the invention features a dispensing instrument that includes a source of organisms or large objects, a sensing zone responsive to presence of organisms or objects, a detector directed toward the sensing zone, and a first switched source of fluid having an output directed toward a location downstream from the detector and having a control input responsive to the detector.

In preferred embodiments, the switched source of fluid can include a source of compressed gas and an electrically operated valve, such as a solenoid valve, to interrupt a gas stream from the source of compressed gas. The switched source of fluid can be operative to interact with a fluid stream from the detector with sufficient force to convert fluid in the detector fluid stream into a droplet spray. The switched source of fluid is not contained within any flow chamber so as not to introduce fluidic instabilities. The switched source of fluid can be responsive to a delayed detection signal from the detector. The dispensing fluid switch can be operative to repeatedly leave predetermined amounts of detector fluid stream fluid undiverted. The dispensing instrument can further include a second switched source of fluid positioned to divert fluid left undiverted by the first switched source of fluid.

In a further general aspect, the invention features a dispensing instrument that includes means for providing a fluid stream carrying objects, the means for providing being located within a flow chamber, means for detecting the presence of the objects in the fluid stream, the means for detecting being located downstream from the means for providing, and first means for selectively directing a gas stream toward the fluid stream to divert portions of the fluid, the means for selectively directing being located downstream from the means for detecting, outside of the chamber, and being responsive to the means for detecting.

In preferred embodiments, a second means can be provided for selectively directing an output of the first means for selectively directing, relative to a first container to thereby dispense portions of the fluid stream into a second container. The means for selectively diverting can be for including only a predetermined amount of fluid with each of the objects selected.

In another general aspect, the invention features a dispensing method that includes feeding objects through the center of a sensing zone with a carrier fluid, detecting the presence of the objects, diverting at least some of the carrier fluid based on the step of detecting, and collecting ones of the objects remaining in portions of the carrier fluid.

In preferred embodiments, the step of diverting can include a step of converting the carrier fluid into a droplet spray. The step of diverting can take place for a predetermined period of time for each of the objects. The step of diverting is physically removed from the step of detecting so as to avoid introducing fluidic instability. The method can further include a step of sorting the objects into a plurality of categories after the step of diverting and the step of collecting can collect the objects in a plurality of different containers. The method can further include the step of exposing the objects collected in the step of collecting to a pharmaceutical agent. The step of dispensing the objects can include dispensing predetermined numbers of the objects into each of a number of containers. The step of feeding can feed reference particles with the objects. The step of dispensing can include dispensing only objects having a particular characteristic into a container.

Systems according to the invention can help to accelerate and reduce the cost of pharmaceutical development. By rapidly sorting and depositing large numbers of live populations with particular characteristics, a sorting instrument according to the invention can allow many compounds to be tested on the sorted organisms in a given time period. By permitting particular types of multicellular organisms to be selected from large populations, individuals with infrequent mutations can be collected and studied more quickly. By permitting the selection and accurate deposition of large microspheres bearing test compounds the test organisms and test compounds can be rapidly and accurately combined. As a result, more experiments can be performed in the same amount of time, and these experiments can be performed at a lesser expense.

BRIEF DESCRIPTION OF THE DRAWINGS

FIG. 3 is a diagrammatic cross-section of a flow cell for use in the system of FIG. 2;

FIG. 4 is a diagram illustrating the alignment of elongate sample organisms in the sheath flow cell of FIG. 3;

FIG. 4A is an axial cross-section of a sensing chamber of a flow cell and detector for the system of FIG. 2;

FIG. 4B is a longitudinal cross-section of the sensing zone of the flow cell and detector for the system of FIG. 2;

FIG. 6 is a longitudinal cross-sectional diagram illustrating the relationship between a nematode and an optical sensing zone of a sheath flow cell for the system of FIG. 2;

FIG. 7 is diagrammatic plot of voltage against time for a light blocking signal in the system of FIG. 2;

FIG. 8A is a block diagram of a first alternative fluid drive system for the system of FIG. 2;

FIG. 8B is a cross-sectional diagram of a syringe for the system of FIG. 8A;

FIG. 9 is a block diagram of a second alternative fluid drive system for the system of FIG. 2;

FIG. 10A is a diagrammatic plot of voltage against time for a light blockage signal produced by an adult nematode and a coincident egg;

FIG. 10B is a diagrammatic plot of the derivative of the signal of FIG. 10A;

DETAILED DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein specifically to provide a device for selecting and depositing elongate multicellular organisms or other large objects using a high speed fluidic switch and controlled fluid stream to deflect unselected organisms.

This application refers repeatedly to large objects and multicellular organisms. By "large" is meant objects or organisms significantly larger than those analyzed and sorted by a traditional electrostatic sorter which normally sorts objects on the order of 10 $\mu$m diameter with droplets on the order of 50 $\mu$m diameter. Large objects are larger than 50 $\mu$m diameter and preferably have at least one dimension ranging between 70 and 500 $\mu$m or larger. The droplet sizes employed with the current invention are at least 100 $\mu$m in diameter and preferably 1 mm in diameter. Thus, "large" objects are at least one order of magnitude larger than those handled by traditional electrostatic sorters.

Figure 1:
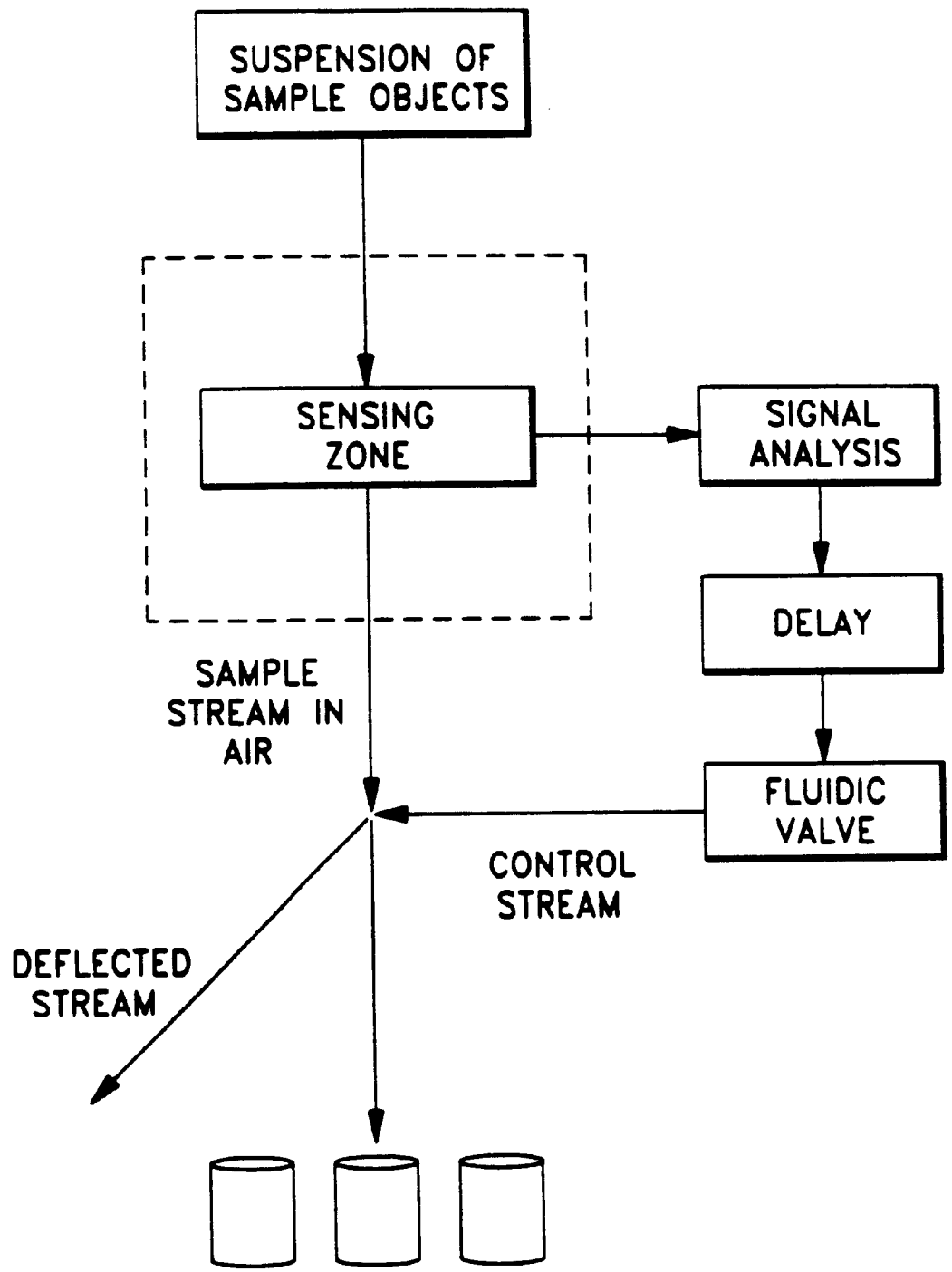
FIG. 1 is a general diagrammatic sketch of the analysis and dispensing system of the present invention.

FIG. 1 shows an extremely diagrammatic representation of the instrument of the present invention. Attention should be paid to the salient elements of the present invention. Large sample objects from a source 46 are centered and aligned in a fluid stream in a flow chamber 16 by hydrodynamic focussing. Detectors detect characteristics of sample objects in the flow stream. Down stream from the detectors and physically isolated from the detectors to avoid propagation of fluidic instabilities a control stream of fluid under the control of an electronic valve 20 diverts portions of the sample stream not desired. Sample stream portions containing sample objects meeting predetermined characteristics are not diverted and pass into one of a plurality of indexable containers 82.

Figure 2A:
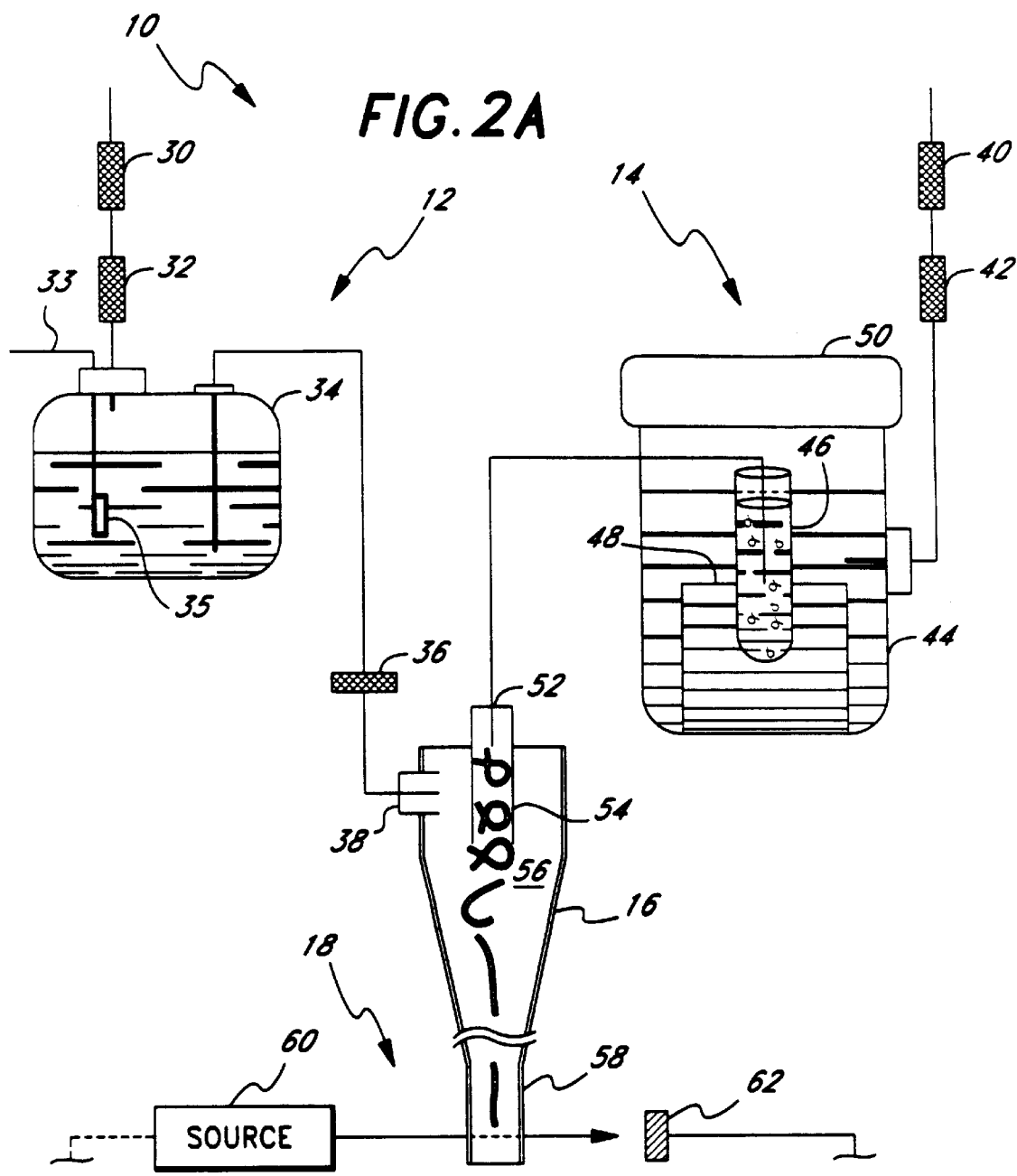
FIG. 2 is a block diagram of a large object dispensing system according to the invention.
Figure 2B:
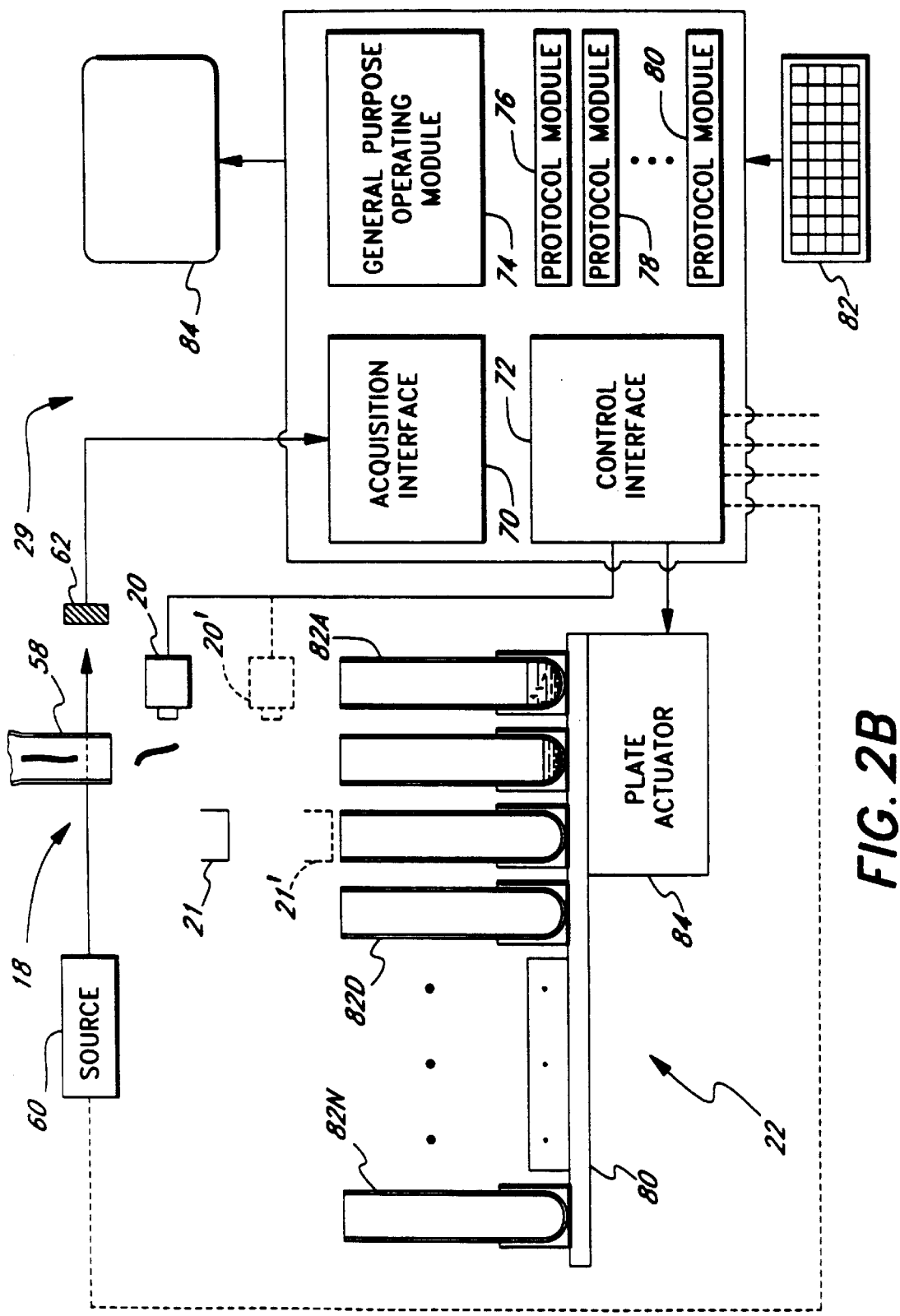

Referring to FIG. 2, a dispensing system 10 for elongate, multicellular, invertebrate animals, such as nematodes, or for other large objects includes a sheath fluid drive system 12, a nematode fluid drive system 14, a sheath flow cell 16, a detection system 18, a sorting actuator 20, a container actuation system 22, and a diagnostic and control processor 24. The sheath fluid drive system includes a first stage regulator 30 that has an input opening for a pressurized gas source, such as a 25–30 psig nitrogen or a compressed air source. A second stage regulator has an input connected to the first stage regulator and an output delivering gas at a regulated pressure to a sheath fluid reservoir 34. An electronic level sensor 35 controls a sheath fluid input line 33 to maintain a constant level in the reservoir. A particle filter 36 is connected between an output of the sheath fluid reservoir and an input opening 38 of the flow cell to prevent any particles in the sheath fluid from passing into the flow cell.

A sample fluid drive system similarly includes a first stage regulator 40 connected to a pressurized gas source, such as a 25–30 psig pressurized nitrogen or air source. A second stage regulator 42 is connected between the first stage regulator 40 and an input of a sample pressure vessel 44, which is sealed with a clamped cap 50. The sample pressure vessel 44 includes a sample storage reservoir 46 mounted on a mixing device 48. The multicellular sample organisms such as nematodes are placed into the sample storage reservoir 46. The mixing device 48 can be a magnetic stirrer that includes blades that produce an upwelling in the fluid containing the suspended sample organisms or objects. An outflow line is provided between the sample storage reservoir 46 and a sample feed input 52 of the flow cell 16. The flow cell 16 includes a sample feed chamber 54, a sheath fluid chamber 56, and a sensing chamber 58. To operate effectively in commercial settings, the dead volume in the outflow line and flow cell should be low, such as less than 500 microliters.

The detection subsystem 18 includes a source 60 and a detector 62 placed on either side of the sensing chamber 58. The source can be an optical source, such as a laser (e.g., a semiconductor laser or a helium-neon (HeNe) laser). The source can also be a non-optical source, or it can even be omitted, such as when chemiluminescent, phosphorescent or radioactive markers are used on the organisms or objects themselves. The preferred embodiment uses an optical detector but may be readily supplemented with an additional detector for non-optical radiation, magnetism or other physical properties that may distinguish organisms or other analyzed objects. An optical detector can be a photodiode, or any other suitable type of optical or non-optical detector. A second, off-axis detector can also be provided, such as to detect light scattered from the sensing chamber at right angles. The off-axis detector is located generally perpendicular to an illumination axis of the source.

The sorting actuator 20 can be a switched source of fluid. An example would be a high-speed valve that switches air from a pressurized air source. High-speed valves made for ink-jet printing applications have appropriate characteristics. Suitable valves of this type include the Inka series (e.g., INKA4004212H) miniature solenoid valves, available from the Lee Company of Westbrook, Conn. These valves can operate from a low voltage source at rates of up to 1200 Hz, easily allowing the system to handle rates of 50 sample organisms per second or better, although rates of 10 or 20 organisms per second are relatively satisfactory for dispensing into 96-well plates. An extremely important aspect of the current invention is the placement of the actuator 20. The objects to be analyzed and deposited are oriented and preferably detected within a flow chamber; the actuator 20 must be placed down stream and outside of this flow chamber so that the diversion process is physically isolated from the chamber. Otherwise fluidic disturbances introduced by the diversion process would prevent analysis and selection of large objects at any reasonably high speed.

A gutter 21 is placed across from the actuator in such a way as to catch animals or objects that are deflected when the actuator is in its open state. In summary when the actuator is closed, the sample stream containing the sample organisms passes through the flow cell and into the collection container such as a microwell of a microtiter plate. When the actuator is open, the sample stream is diverted in the gutter 21 and does not reach the microwell. Clearly, such a deflection process operates optimally when the deflection occurs outside of and away from the flow chamber.

The container actuation system 22 includes a plate 80 (e.g., a microtiter plate) that includes a plurality of containers 82A . . . 82N (e.g., microwells) into which the system dispenses the sample organisms. The plate is mounted on a plate actuator 84 that includes a drive mechanism. The drive mechanism successively places the containers of the plate in the outflow path of the flow cell 16. The drive mechanism is under control of the diagnostic and control processor 24.

The diagnostic and control processor 24 includes an acquisition interface 70 having an input responsive to the detector 62. It also includes a general-purpose operating module, and one or more protocol modules 76, 78, 80. A keyboard 82 (or similar data input means) is operationally connected to the computing system that also drives a display 84. The diagnostic and control processor 24 also includes a control interface 72 that can provide an actuator control signal to the actuator 20 and a source control signal to control the source 60.

The diagnostic and control processor 24 can include dedicated hardware, special-purpose software running on a general-purpose computer processor, or a combination of the two. The decision to implement any specific functionality using a particular approach will be based on a number of economic and technical considerations and tradeoffs. For example, the acquisition interface 70 can filter and condition the signal received from the detector 62 using either analog circuitry or software signal processing routines or a hardware DSP (digital signal processor). The objectives of the system may also be met by variants of the architecture shown. For example, the plate actuator might be controlled by a controller that is independent of the diagnostic and control processor, such as a dedicated fill-level detector. Changes may also be made to the hydraulic portions of the system without impacting its functionality or objectives as long as certain points are observed: the fluidic diversion process must be physically isolated from the orientation and detection processes. An optimal method of achieving this isolation is to place the fluidic diversion downstream and outside of the flow chamber where the fluidic diversion operates on a sample stream in air. This makes it impossible for fluidic instabilities caused by the diversion process to be transmitted upstream into the detection zone where they would disrupt the entire process.

Figure 11:
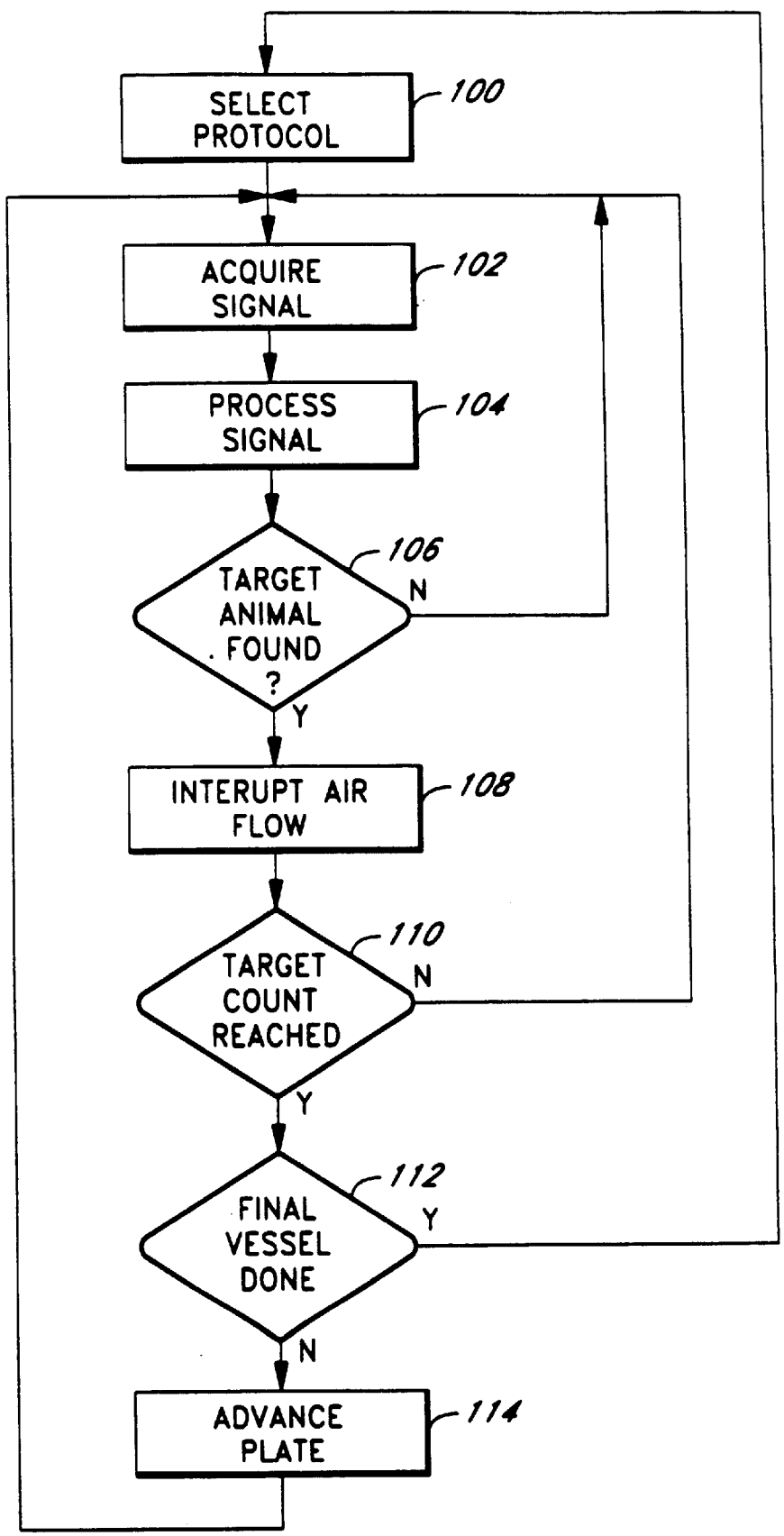
FIG. 11 is a flow chart illustrating the overall operation of the system of FIG. 1.

Referring to FIGS. 2 and 11, operation of the system 10 begins with user selection of a protocol for a particular dispensing operation (step 100). This can be accomplished by calling one of the protocol modules 76, 78, 80, which handle different types of operations. For example, a simple counting module allows the system to dispense a fixed number of sample organisms into each of the containers 82A . . . 82N. A more sophisticated counting operation may count the organisms while eliminating undesirable material such as eggs, etc. Even more elaborate protocols can detect the characteristics of individual organism or particles and only select those with particular developmental, genetic or other characteristics, such as by detecting a radioactive or fluorescent marker on the organism or particle or by detecting a particular size or shape of the object. Still more complex protocols allow parts of the system to sort objects into two or more subpopulations, while also rejecting undesirable material (e.g., organisms of the wrong stage or type or debris or particles of the wrong size, etc.).

The first step specified by the protocol is to acquire from the detector 62 a signal that represents the interaction between light from the source 60 and sample objects in the sensing chamber 58, when an optical detection scheme is employed (step 102). The diagnostic and control processor 24 then performs signal processing operations, such as filtering, on the acquired signal to enhance the detection of sample object (step 104). The computer system tests the processed signal for a detection condition, until a target object is found (step 106). The detection condition may be different for different protocols. For example, the computer system may only seek animals without coincident eggs, or other debris. Alternatively, it may require that a sample organism or particle meet particular size or shape criteria.

Different types of detectors may also be associated with different detection conditions. For example, a radiation counter may need to sense a radiation level threshold to detect a radioactive marker in an animal. A magnetic sensor may detect magnetic particles used in combinatorial chemistry. Alternatively, an optical detector may need to sense a particular level of light to detect a bioluminescent, chemiluminescent, phosphorescent or fluorescent marker. When the computer finds a target object that meets the proper criteria, the valve of the sorting actuator 20 interrupts the gas flow that is directed at the sample stream exiting the flow cell 16 (step 108) for a predetermined period of time corresponding to the target object's length. This prevents the target object from being accidentally blown into the gutter 21. If this is not the last object needed in a particular container, the system continues to acquire, process, and test the signals either until another target object is detected, until a timer expires, or until an error signal is encountered (step 110). When the system reaches the target count for the container, and other containers remain to be filled (step 112), the control interface 72 of the computer system 24 instructs the plate actuator 84 to advance the plate 80 (step 114). After the plate has been advanced, the signal is again acquired, processed, and tested to select objects to dispense into the next container.

More complex protocols can operate a pair of sorting actuators, 20', or a multi-level actuator, to direct target objects to three or more destinations, such as either a vessel, a first gutter 21, or a second gutter 21' placed downstream from the first gutter 21 (see dashed lines in FIG. 1). In this type of configuration, the system can readily separate a population of sample objects into two subpopulations, while also rejecting undesirable material. Again, both sorting actuators are down stream from and outside of the flow chamber so that the sorting process cannot introduce fluidic instabilities.

Referring to FIGS. 3 and 4, the flow cell 16 is constructed to center and align the elongate sample organisms in the detection chamber. Differing velocities within the fluid in the flow cell cause the organisms to become aligned with the flow direction. This happens because fluid flowing further from the center of the cell (e.g. 86) moves at a faster rate than fluid flowing closer to the center of the cell 87 (e.g. fluid along line 88). This velocity difference causes the organisms to become aligned in almost all instances. Although occasional folding of the sample organisms may occur, such organisms can be rejected by the sorting mechanism.

The aligning effect of the flow cell 16 can be pictured by imagining a strand of limp spaghetti being moved through water by an intersecting smooth rod. The spaghetti will virtually always straighten out and slip off the rod because of the unbalanced drag on the longer end of the strand. The only case where this does not occur is when the rod is exactly in the middle of the strand.

The flow cell 16 is configured to cause the sheath flow liquid to flow past the opening of the sample organism feed tube 54 at a rate that maintains the Reynolds number of the sheath fluid below about one hundred. Keeping the Reynolds number below about one hundred ensures that the flow is laminar and without Van Karman instability, which helps to keep the sample organisms centered in the sensing chamber. The Reynolds number is computed by treating the edge 55 of the opening of the sample flow tube 54 as a bluff object. The hydrodynamics of bluff objects are discussed in, for example, sections 9.1–9.2 of "Principles of Heat Transfer," by Frank Kreith, International Textbook Company, Scranton, Pa., 1966, which is incorporated herein by reference.

It is important to center the sample organisms in the flow stream because the velocity of the fluid is not the same across the diameter of the sensing chamber 58. Since fluid viscosity, density, and velocity used in the system are selected to give rise to laminar flow, the velocity profile is parabolic in the detection cell. This means that the velocity is a maximum and roughly constant over a reasonably broad region of the center of the cell, and is zero at the boundary between the fluid and the cell wall. As a result, centered sample organisms will all flow at a single velocity and not pass one another or "bunch" together. If the organisms were not centered, those near the wall could flow more slowly than those at the center, which could result in "coincidence counting" (e.g., more than a single organism at a time passing the sensing zone) even when the dilution of organisms in the sample organism chamber has been calculated to avoid such coincidence. Lack of centering could also mean that, after detection, an organism near the wall might travel so slowly that other organisms could pass it, enter the fluid space that was reserved for the slower organism, and be incorrectly dispensed. There is essentially no mixing of the sample fluid with the sheath fluid until the two are dispensed into the container.

Referring to FIGS. 5A, 5B, and 6, the sensing chamber 58 has a square cross-section. This shape makes the cell easy to align optically, and it should stay in proper alignment for months without operator intervention. The shape of the beam in the focal region, or "sensing zone," is extremely important. The beam should be broad in the x direction, (i.e., along the beam) and narrow in the z direction (i.e., along the horizontal axis). From the standpoint of optical kinematic design, the only difficult alignment direction in the system is in the x direction, which is why a broad, forgiving beam is used in this dimension. A sharp focus (FIG. 5B) in the z dimension permits the system to measure a sample organism along its axis (length) by measuring its "time of flight" through the sensing zone. In one embodiment, optimized for organisms approximately 70 $\mu$m in diameter, the optical sensing zone is 20 $\mu$m thick in the z direction, and the sensing chamber is 300 $\mu$m wide in the x and y directions. The relative positions of the source 60, the sensing chamber 58, and the detector 62 cause the detector to measure light blockage. When a sample organism passes into the sensing zone, some light will be scattered out of the beam (major effect), while some light will be absorbed (minor effect). Both of these effects cooperate to lower the light level at the detector when an organism passes through the sensing chamber. The drop in the light passing from the source to the detector can be readily registered as a count by an electronic threshold detector, and passed onto the processor 24, or even to a less sophisticated device, such as a counter. Noise generated in the laser and the detector should not be a consideration in the detection of objects as large as multicellular sample organisms.

The system can use detector pulses to simply count and activate a dispensing command, but pulses can also be used to size the sample organism. Sizing is not quantitatively essential in a sample population that has been purified by a gradient, but it is nevertheless important to set a size threshold to separate background debris from the target organisms. The presence of an object is sensed by a drop in voltage from the detector, which persists as long as the object is in the sensing zone (see FIG. 7 where the width 93 of the detected pulse 91 is representational of organism dwell time in the sensing zone). If the object speed (i.e., the fluid speed at the center of the sensing cell) and the time duration of the negative-going pulse are known, the processor can calculate the length of the object (particularly valuable with elongated multicellular organisms).

Fluid speed can be maintained by precision mechanical design, or, less expensively, by seeding the fluid with a very low concentration of small polystyrene microspheres and then detecting the light extinction signal from these microspheres while the sample organisms are being counted. The organisms and microspheres can be made to have completely distinguishable light extinction signals that can be acted upon differently by the computational electronics, even if a sample objects and a microsphere pass through the sensing zone together. The introduced microsphere's time of flight is not used to regulate the fluid speed, which tends to be expensive and difficult, but only to change the computational parameters used to calculate the sample organism length. The biological effect of the plastic microspheres may be detrimental to certain species or to downstream processes, and should therefore be evaluated carefully before implementation.

If there is a good biological correlation between the length and diameter of the organism, the time-of-flight length measurement may yield sufficient size information. If this correlation does not exist in the population of interest and microspheres cannot be used, the organism's diameters can be measured by a second detector positioned off-axis in the x-direction. This detector will register an electronically positive-going, light-scatter pulse. The amplitude, as opposed to the duration, of the electronic pulse can be related in real time to the diameter of the sample organism via a set of light scattering equations stored in the computer system. The light extinction signal from the on-axis detector and the light scatter signal from the off-axis detector can be combined by the computer to give a real-time calculation of all dimensions of the sample organism. Of course, different types of organisms (e.g., nematodes versus fruit fly larvae) will require somewhat different prestored scattering information.

Referring to FIGS. 10A and 10B, the light scattering theory usually applied to objects in flow cytometry is termed Rayleigh-Gans, or anomalous diffraction, theory. It applies to objects that are large compared to the source wavelength and that exhibit a low refractive index relative to the surrounding medium, which is water in this case. Using this theoretical treatment as a first approximation, the processor can use the assumption that light blockage signals follow the area of geometric shadow for the sample organisms. In the case of nematodes the sample population may include adult worms, larvae, and eggs. Under this assumption, the temporal signal for an adult nematode and an egg together would appear as shown in FIG. 10A. Standard electronic methods can be applied to such a signal to distinguish between an adult nematode signal and one that is coincident with an egg. For example, computing the derivative of a blockage signal, as shown in FIG. 10B, allows an adult-egg coincidence to be more readily detected; for example, an odd number of pulses in a pulse train is indicative of a coincidence. It is noted that even though the nematodes are too large in diameter to be accurately handled by Rayleigh-Gans, or anomalous diffraction, theory, this treatment may be sufficient for many purposes. More detailed models could also be developed to obtain more information about the nematodes or other multicellular sample organisms. Overall, optical detection is particularly versatile in measuring the size and shape of sample organisms or other large objects.

Referring to FIGS. 8A, 8B, and 9, although the fluid design presented in FIG. 2 is inexpensive and easy to clean, other fluid designs also present advantages. In a first design alternative, the sheath vessel is pressurized, and the sample (nematode) flow is driven by a syringe pump 90 (see FIG. 7A). The cost of such a system is higher and clean-out may be more difficult, but this alternative exhibits greater flow stability which allows the flow velocity to be more tightly regulated, which may make microspheres unnecessary while providing more accurate size discrimination. The syringe barrel in this alternative design can be rotated to keep the sample organisms in suspension (see FIG. 7B.) This can be accomplished most readily by rolling the barrel back and forth (oscillatory rotation) because there is no need for a rotating fluid seal. A ribbed interior to the syringe barrel may also facilitate mixing.

In a second alternative approach, a syringe 92 is provided with a rigid sample (nematode) chamber 94 through a system of check valves 96, 98 (see FIG. 9). In this alternative system, sample organisms are not drawn actually into the syringe barrel, but are instead held in the rigid chamber 94. A sample organism-friendly fluid without organisms is drawn into the syringe periodically through the check valves and mixing takes place outside the syringe as the fluid enters the chamber 94 (which is equipped with mixers to keep the organisms in suspension. This alternative method of operation does not require syringe changes to replenish the organism supply. Both of these alternative approaches can use ordinary disposable plastic syringes.

The alternative designs may be less likely to produce significant pressure transients in the fluid lines. Such pressure transients could slow down or shut off sample flow in the flow cell all together and result in a period during which organisms are not centered and not oriented. In the fluidic system presented in FIG. 2, methods of stirring the organisms should be chosen to keep them in suspension without introducing significant pressure transients. Magnetic stirrers producing upwelling are available, and may be the simplest solution. A roller bottle or Archimedes screw configuration does not introduce fluidic noise and provides effective suspension of the sample organisms. The fluid lines in the storage vessel should not move during operation, and, for this reason, the flow cell should remain stationary while the plate moved to effect changes in container position. While very stable, the sample containers in the alternative embodiments must be ultimately refilled, which can result in down time for the system as compared to the device of FIG. 2 where the sample can rapidly be replenished.

Figure 12:
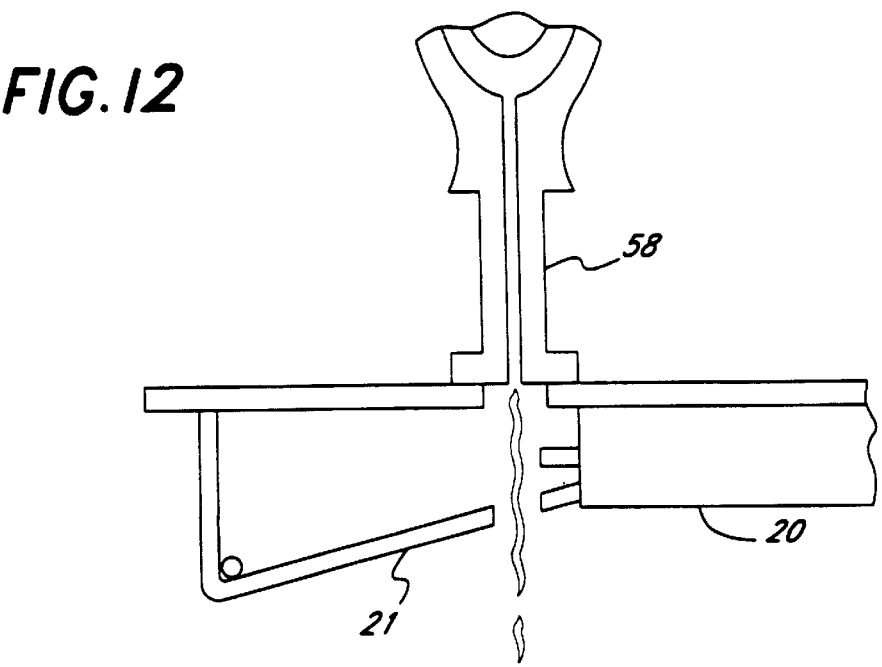
FIG. 12 is a diagrammatic cross-section of sections of an embodiment of the large object dispensing system of FIG. 1.

Referring now to FIG. 12, one embodiment of the sensing chamber 58 can be made of an upright quartz rectangular parallelepiped with a 250 $\mu$m diameter capillary passing through its longitudinal axis and defining a sensing zone. Note that although the square cross-section is preferred, it is also possible to use other sensing chamber geometries, or even to omit the sensing chamber walls altogether, leaving only an open sensing zone. The fluid output of the actuator 20 is preferably located less than about one centimeter below the outlet of the capillary and at about one millimeter from the undisturbed position of the liquid flow. It is important that the actuator 20 be located so as not to introduce fluidic instabilities into the flow stream. The one millimeter dimension has been found to be optimal for this embodiment, because it appears to result in atomization of the fluid rather than a deflection of the flow, which tends to result in flow disturbances. The actuating fluid flow direction is aimed substantially at right angles to the sample fluid flow.

Figure 13:
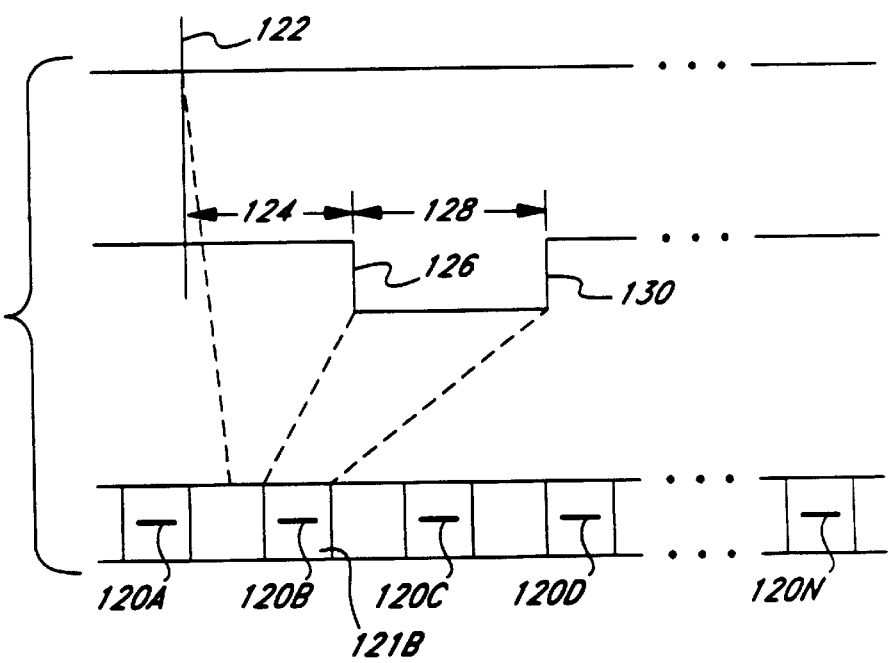
FIG. 13 is a diagram illustrating nematode flow over time and corresponding electronic signals for one nematode on a different scale, for the dispensing system portions of FIG. 12.

Referring to FIG. 13, the flow of sample organisms (here nematodes) 120A, 120B, . . . 120N over time tends to be irregular. Simply dispensing groups of them while leaving the actuator valve deactivated may result in different volumes of liquid being conveyed with different groups. For this reason, the valve is deactivated only when one of the nematodes is present. When a nematode (e.g., 120D) is detected in the capillary, a peak detect signal 122 is derived from the output of the detector. After a travel period 124 that is related to the travel time of the nematode from the detector beam to the actuator and to the response time of the actuator, the actuator is turned off (edge 128). The actuator is then kept off for a pass period 126, turned on (edge 130), and left on until a peak detect signal is detected for the next nematode. This timing allows the nematode and a predetermined amount of surrounding liquid 121B to pass into the vessel below, but prevents excess liquid from entering the vessel. In one embodiment the travel period is four microseconds, and the pass period is adjustable from four to ten microseconds. The system can also be programmed to pass more than one nematode in each pass period. Typically, the organism is encased in a cylindrical fluid segment that is several millimeters in length and approximately 0.2 millimeters in diameter. The volume of the fluid segment containing the organism is of the order of magnitude of one microliter or slightly less. Therefore, if only one or a few organisms is dispensed into each microwell, the dilution effect on a test sample of 50–100 microliters is negligible.

Ensuring that a only predetermined amount of liquid accompanies a population of sample organisms is beneficial for several reasons. It may be difficult to accurately meter similar doses of test substances into different containers if there are different amounts of liquid in each of the containers. Longevity and activity of the sample organisms may also be affected, since increasing the amount of liquid in each container increases the volume-to-surface area ratio for the container, which can affect oxygen uptake for the sample organism. Making large, single, elongate droplets that each contain a single sample organism also helps to avoid injury to the organism as it is dispensed.

Other methods may also be suitable for diverting the fluid flow. Such methods may include the use of electrostatic, piezoelectric, ferrofluidic, or other suitable fluid switches. In order to keep the sample organisms alive, however, these methods must be carefully tailored. For example, experiments with electrostatic switching arrangements appear to indicate that exposing multicellular organisms such as nematodes to high frequency mechanical vibrations used to break-the flow stream into variably charged droplets and to the high intensity electric fields used to deflect those droplets is frequently lethal to the organisms. As a result, the electric field levels and vibration levels for this type of switch would have to be reduced at the expense of other system parameters to act as a suitable switch for multicellular organisms. Even then the analysis presented above indicates that the great fall distances required for adequate deflection of large (e.g., greater than about 50 $\mu$m ) droplets essentially precludes the use of electrostatic sorting methods with large objects. Ferrofluidic additives may also prove detrimental to the sample organisms or interact with agents to be tested on the organisms, so the effect of any such additive must be carefully evaluated before its selection. Further, the addition of a ferrofluidic material adds to expense and experimental complexity. Piezoelectric valves, such as those presented in "A New Fluid Switching Flow Sorter," by J. Duhnen et al., Histochemistry 77:117, (1983), introduce substantial shock waves into the fluid and may therefore also result in injury to multicellular organisms. The transducer's mechanical output level, the geometry of the sorter, and the switching margin must therefore be adjusted to suit the population to be sorted. For the reasons discussed above, the use of a fluid valve is presently contemplated to be the most appropriate approach to diverting the fluid flow for multicellular organisms. Again, it is important that the fluid valve be physically isolated from the flow orientation and detection systems to avoid introducing fluidic instabilities that would impair orientation and detection. In many of the described examples the diverting fluid is a gas, namely air. It is clear that other gases such as nitrogen or argon can be readily substituted for air. It is also contemplated that other fluids such as liquids may be used in the present invention.

Other types of objects can be sorted using techniques described in this application, elongate, multicellular animals are of particular interest. For example, live fruit fly larvae (*Drosophila melanogaster*) have been successfully dispensed using these techniques. It is also believed that these techniques are well suited to dispensing and sorting the elongate embryos of zebrafish (*Danio rerio*). Obviously other multicellular organisms of similar sizes such as additional nematode or other worms, insect larvae, other arthropod or molluscan or vertebrate larvae are equally useable in the present invention. Nor should embryos of various plants be overlooked for testing compounds of agricultural rather than pharmaceutical use. Apart from multicellular organisms, large microspheres used in combinatorial chemistry to produce libraries of test compounds are preferred objects to be analyzed and deposited by the instrument of the present invention.

In addition to the equivalents of the claimed elements, obvious substitutions now or later known to one with ordinary skill in the art are defined to be within the scope of the defined elements. The claims are thus to be understood to include what is specifically illustrated and described above, what is conceptually equivalent, what can be obviously substituted and also what essentially incorporates the essential idea of the invention. Those skilled in the art will appreciate that various adaptations and modifications of the just-described preferred embodiment can be configured without departing from the scope and spirit of the invention. The illustrated embodiment has been set forth only for the purposes of example and that should not be taken as limiting the invention. Therefore, it is to be understood that, within the scope of the appended claims, the invention may be practiced other than as specifically described herein.

What is claimed is:

1. An instrument comprising:
   a detector;
   a structure adapted to provide a first control stream; and
   a first fluidic valve located downstream of the detector, wherein the first fluidic valve is in operative relationship with the detector and the structure so that, when a continuous fluid stream carrying sample objects is introduced into the instrument, the continuous fluid stream:

(i) flows past the detector so that sample objects in the continuous fluid stream are detected and a detection signal is generated, and then (ii) flows past the first fluidic valve, which responds to the detection signal by interrupting the first control stream that operationally intersects the continuous fluid stream and deflects the continuous fluid stream, thereby allowing lengths of the continuous fluid stream containing detected sample objects to flow past the first fluidic valve undeflected by the first control stream.

2. The instrument of claim 1 further comprising:

a source located upstream of the detector, wherein the source is adapted to contain sample objects in a fluid suspension and has an output opening that produces a continuous fluid stream carrying sample objects when the source contains sample objects in a fluid suspension.

3. The instrument of claim 2 further comprising:

a flow chamber having an input opening in fluidic communication with the output opening of the source and having an output opening, wherein the flow chamber centers and aligns sample objects in a continuous fluid stream when a continuous fluid stream carrying sample objects is flown there through.

4. The instrument of claim 3 further comprising:

a sensing chamber having an input opening in fluidic communication with the output opening of the flow chamber and having an output opening, wherein the detector is adapted to detect sample objects in the sensing chamber when a continuous fluid stream carrying sample objects is flown there through.

5. The instrument of claim 4, wherein a relationship between the flow chamber and the output opening of the source is defined to maintain a Reynolds number of about one hundred or less between the output opening of the source and a volume of the sensing chamber.

6. The instrument of claim 4 further comprising:

an illumination source directed toward the sensing chamber, wherein the detector is an optical detector.

7. The instrument of claim 6 further comprising:

a processor in operative relationship with the detector that determines the length of at least one of the sample objects by measuring the time that at least one of the sample objects takes to pass between the detector and the illumination source when a continuous fluid stream carrying sample objects is introduced into the instrument.

8. The instrument of claim 6, wherein the detector is an on-axis detector that is located across the sensing chamber from the illumination source along an illumination axis of the illumination source.

9. The instrument of claim 8 further comprising:

an off-axis detector, located generally perpendicular to an illumination axis of the illumination source.

10. The instrument of claim 6, wherein the illumination source is a focused low-power laser.

11. The instrument of claim 6, wherein the sensing chamber has a width of about 10 to 40 microns.

12. The instrument of claim 6, wherein the sensing chamber is defined by a set of walls having a square cross-section.

13. The instrument of claim 6, wherein the output opening of the source is separated from the input opening of the sensing chamber by a total conduit volume of less than about 500 microliters.

14. The instrument of claim 3, wherein the flow chamber further includes an input opening for a sheath fluid.

15. The instrument of claim 1 wherein the structure includes a source of compressed gas and the first control stream originates from the source of compressed gas.

16. The instrument of claim 1 further comprising:

at least one container located downstream of the first fluidic valve, wherein the at least one container is adapted to receive lengths of the continuous fluid stream containing sample objects that pass undeflected by the first control stream when a continuous fluid stream carrying sample objects is introduced into the instrument.

17. The instrument of claim 16 further comprising:

a computer system in operative relationship with the detector and the first fluidic valve, wherein the computer system is adapted to test the detection signal for a detection condition so that, when target objects that meet the detection condition are identified by the computer system, the computer system triggers the first fluidic valve to interrupt the first control stream, thereby allowing lengths of the continuous fluid stream containing target objects to flow past the first fluidic valve undeflected by the first control stream.

18. The instrument of claim 17, further comprising:

a second fluidic valve located downstream of the first fluidic valve, wherein the second fluidic valve is adapted to control a second control stream that is directed at the lengths of continuous fluid stream containing target objects that pass undeflected by the first control stream, wherein the computer system is adapted to test the detection signal for a set of different detection conditions, and wherein the second fluidic valve is in operative relationship with the computer system so that, different lengths of the continuous fluid stream containing different target objects can be sorted into different containers by the second control stream based on the different detection conditions identified by the computer system.

19. The instrument of claim 1, wherein the first control stream operationally intersects the continuous fluid stream with sufficient force to convert the continuous fluid stream into a spray of droplets.

20. An instrument comprising:

means for providing a continuous fluid stream carrying sample objects;

means for detecting the sample objects in the continuous fluid stream, the means for detecting being located downstream from the means for providing;

means for providing a first gas stream, wherein the first gas stream operationally impinges on the continuous fluid stream and diverts the continuous fluid stream; and first means for interrupting the first gas stream, wherein the first means for interrupting is located downstream from the means for detecting, and is in operative relationship with the means for detecting so that, when the means for detecting detects sample objects in the continuous fluid stream, the first means for interrupting responds by selectively interrupting the first gas stream, thereby allowing lengths of the continuous fluid stream containing detected sample objects to pass undiverted by the first gas stream.

21. The instrument of claim 20 further comprising:
means for aligning sample objects in a continuous fluid stream.

22. The instrument of claim 20 further comprising:
means for collecting the lengths of continuous fluid stream containing sample objects that pass undiverted by the first gas stream.

23. The instrument of claim 22 further comprising:
means for testing sample object detection signals from the means for detecting for a detection condition, the means for testing being in operative relationship with the means for detecting and the first means for interrupting so that, when target objects that meet the detection condition are identified by the means for testing, the means for testing triggers the first means for interrupting to selectively interrupt the first gas stream, thereby allowing lengths of the continuous fluid stream containing target objects to flow past the first means for interrupting undeflected by the first gas stream.

24. The instrument of claim 23 further comprising:
second means for interrupting a second gas stream, the second means for interrupting being located downstream from the first means for interrupting, the second means for interrupting being adapted to control a second gas stream that is directed at the lengths of continuous fluid stream containing target objects that pass undeflected by the first gas stream, wherein the means for testing is adapted to test sample object detection signals from the means for detecting for a set of different detection conditions, and wherein the second means for interrupting is in operative relationship with the means for testing so that, different lengths of the continuous fluid stream containing different target objects can be sorted into different means for collecting by the second gas stream based on the different detection conditions identified by the means for testing.

25. The instrument of claim 23, wherein the first means for interrupting includes only a predetermined amount of fluid with each target object that is identified by the means for testing.

26. The instrument of claim 20, wherein the means for providing provides live elongate, multicellular animals as the sample objects, and wherein the gas stream is operative to divert the multicellular animals while leaving the viability of the multicellular animals unimpaired.

27. The instrument of claim 20, wherein the means for providing provides micro spheres having a dimension of between about 70 and 500 microns as the sample objects.

28. A method comprising steps of:
providing large objects in a continuous carrier fluid;
passing the continuous carrier fluid and large objects through a sensing chamber;
detecting the presence of large objects in the sensing chamber;
diverting the continuous carrier fluid with a switched control stream that is located downstream of the sensing chamber; and
collecting at least one large object by temporarily ceasing to divert the continuous carrier fluid based on the step of detecting.

29. The method of claim 28 further comprising a step of centering and orienting the large objects in the continuous carrier fluid before the step of passing the continuous carrier fluid and large objects through a sensing chamber.

30. The method of claim 29, wherein the step of centering and orienting the large objects in the continuous carrier fluid includes a step of conveying a sheath fluid past a nozzle.

31. The method of claim 30, wherein the step of conveying is performed wit a Reynolds number of about one hundred or less.

32. The method of claim 28, wherein the step of diverting includes a step of converting the continuous carrier fluid into a spray of droplets.

33. The method of claim 28, wherein the step of diverting is temporarily ceased for a predetermined period of time for each of the large objects that is collected.

34. The method of claim 28 further comprising a step of illuminating the sensing chamber, wherein the step of detecting detects light from the step of illuminating.

35. The method of claim 28, wherein the step of detecting employs an on-axis detector and an off-axis detector and combines signals from these detectors.

36. The method of claim 28 further comprising a step of sorting the large objects into a plurality of categories following the step of diverting.

37. The method of claim 36, wherein the step of collecting collects the categories in a plurality of different containers.

38. The method of claim 28, wherein the large objects are multicellular organisms, the method further comprising a step of exposing the multicellular organisms collected in the step of collecting to a pharmaceutical agent.

39. The method of claim 28, wherein the step of collecting the large objects further includes dispensing a predetermined number of large objects into each of a plurality of containers.

40. The method of claim 39, wherein the large objects are multicellular organisms, the method further comprising steps of:
contacting the multicellular organisms dispensed in the step of dispensing to a pharmaceutical agent; and
detecting a change in the multicellular organisms after the step of contacting.

41. The method of claim 40, wherein each of the plurality of containers includes a different pharmaceutical agent.

42. The method of claim 40, wherein each of the plurality of containers includes the same pharmaceutical agent.

43. The method of claim 40, wherein the multicellular organisms are nematode worms.

44. The method of claim 40, wherein the multicellular organisms are fruit fly larvae.

45. The method of claim 40, wherein the multicellular organisms are zebrafish embryos.

46. The method of claim 40, wherein the step of dispensing includes dispensing multicellular organisms having a predetermined characteristic into each of the plurality of containers.

47. The method of claim 46, wherein the step of dispensing includes dispensing only multicellular organisms of a predetermined developmental stage into each of the plurality of containers.

48. The method of claim 46, wherein the step of dispensing includes dispensing only multicellular organisms having a predetermined genetic mutation into each of the plurality of containers.

49. The method of claim 46, wherein the step of dispensing includes dispensing multicellular organisms having a predetermined phenotypic defect into each of the plurality of containers.

50. The method of claim 28, wherein the step of providing provides reference particles with the large objects.

51. The method of claim 28, wherein the step of collecting includes collecting only large objects having a predetermined characteristic into a container.

* * * * *